United States Patent [19]

Wollweber

[11] Patent Number: 4,923,994
[45] Date of Patent: May 8, 1990

[54] 2-CARBOXY-3-CYANO-4-ARYL-PYRROLES

[75] Inventor: Detlef Wollweber, Wuppertal, Fed. Rep. of Germany

[73] Assignee: Bayer Aktienegesellschaft, Leverkusen, Fed. Rep. of Germany

[21] Appl. No.: 349,191

[22] Filed: May 9, 1989

Related U.S. Application Data

[62] Division of Ser. No. 197,065, May 19, 1988.

[30] Foreign Application Priority Data

Jun. 2, 1987 [DE] Fed. Rep. of Germany ....... 3718375

[51] Int. Cl.$^5$ ................. C07D 401/00; C07D 405/00; C07D 207/00
[52] U.S. Cl. .................................... 546/281; 548/517; 548/526; 548/527; 548/532
[58] Field of Search ................ 546/281; 548/517, 527, 548/532, 526

[56] References Cited

U.S. PATENT DOCUMENTS 3,367,944 2/1968 Umio et al. ......................... 548/532

*Primary Examiner*—John M. Ford
*Assistant Examiner*—Robert C. Whittenbaugh
*Attorney, Agent, or Firm*—Sprung Horn Kramer & Woods

[57] ABSTRACT

A process for the preparation of a 3-cyano-4-arylpyrrole of the formula

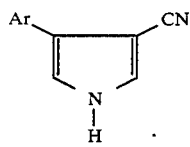 (I)

in which

Ar is optionally substituted heteroaryl or aryl, which comprises (a) reacting an α-cyanoacrylic acid derivative of the formula

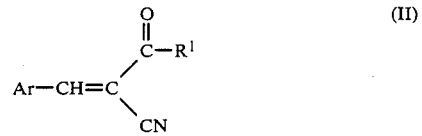 (II)

in which

R$^1$ is amino or alkoxy, with an isocyanoacetic acid ester of the formula

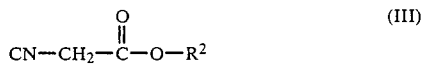 (III)

in which

R$^2$ is alkyl, in the presence of a base thereby to produce a Δ$^2$-pyrroline-2-carboxylic acid derivative of the formula

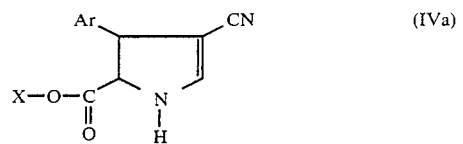 (IVa)

in which

X represents hydrogen or an equivalent of an inorganic or organic cation, and (b) oxidatively decarboxylating the Δ$^2$-pyrroline-2-carboxylic -pyrroline-2-carboxylic acid. The end products are known fungicides and the intermediates IVa are new and themselves fungicidally active.

1 Claim, No Drawings

2-CARBOXY-3-CYANO-4-ARYL-PYRROLES

This is a division of Ser. No. 197,065, filed 5/19/88.

The invention relates to a new process for the preparation of 3-cyano-4-aryl-pyrroles, which are known as fungicides, and also new intermediates for their preparation.

It has been disclosed that 3-cyano-4-aryl-pyrroles are obtained when cinnamonitrile is reacted with p-toluenesulphonylmethyl isocyanide in the presence of sodium hydride (compare DE-OS No. German Published Specification) 2,927,480). However, this process only gives unsatisfactory results with a yield of about 35%. Moreover, it is disadvantageous that the compounds thus obtainable must be purified expensively (compare J6-1030-571). Finally, the reagents sodium hydride and p-toluenesulphonylmethyl isocyanide are both unsuitable for industrial syntheses, the former on account of the high susceptibility to hydrolysis and the attendant danger of fire from the gaseous hydrogen released in the hydrolysis, and the latter on account of the strong irritant action on the skin and eyes and the high instability at elevated temperature (compare EP No. 174,910).

Furthermore, it has been disclosed that 3-cyano-4-aryl-pyrroles are also obtained when α-cyanocinnamic acid esters are reacted with p-toluenesulphonylmethyl isocyanide in the presence of bases and in the presence of copper(II) salts (compare J6-1030-571 or J6-1200-984). The properties of the p-toluenesulphonylmethyl isocyanide also stand in the way of an industrial use in this process.

In addition, it has been disclosed that 3-cyano-4-aryl-pyrroles are also obtained when α-substituted cinnamonitriles are cyclized with ethyl isocyanoacetate in the presence of sodium hydride, and the pyrrole-2-carboxylic acid ester thus obtainable are hydrolyzed using bases and then thermally decarboxylated (compare JP No. 59/212,468). The unfavorable properties of sodium hydride again stand in the way of the industrial utilization of this process. The yields of the cyclization step are also unsatisfactory at 44%.

Furthermore, it has been disclosed that 3-cyano-4-aryl-pyrroles are obtained when phenacylamine derivatives are reacted with suitably substituted acrylonitrile derivatives (compare EP No. 174,910). However, the phenacylamine derivatives necessary as starting compounds are only available through an expensive, multi-step synthesis, in the course of which the unpleasant use of cyanides is also necessary, inter alia.

Furthermore, it has been disclosed that 3-cyano-4-aryl-pyrroles are obtained when the corresponding 3-trifluoromethyl-4-aryl-pyrroles are reacted with ammonia at elevated temperature and elevated pressure (compare EP No. 182,738). However, in this process the 3-trifluoromethyl-4-aryl-pyrroles required as starting materials are also only available through an expensive, multi-step route, wherein the use of moisture-sensitive "Wittig reagents" and costly trifluoroacetic anhydride in the course of this multi-step synthesis additionally makes the industrial feasibility difficult.

Finally, it has been disclosed that 3-cyano-4-arylpyrroles are obtained when 4-cyano-3-aryl-Δ²-pyrrolines are oxidized in the presence of Cu-II salts or iron-III salts (compare EP No. 183,217). In this last process, the preparation of the necessary starting compounds is also multistep and industrially expensive.

It has been found that 3-cyano-4-aryl-pyrroles of the general formula (I)

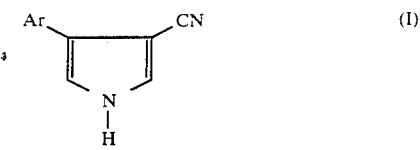

in which
Ar represents in each case optionally substituted heteroaryl or aryl, are obtained when a-cyanoacrylic acid derivatives of the formula (II)

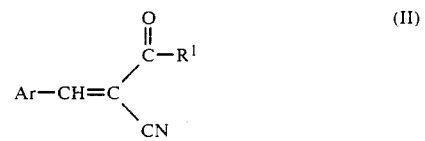

in which
Ar has the abovementioned meaning and
$R^1$ represents amino or alkoxy,
are reacted with isocyanoacetic acid esters of the formula (III)

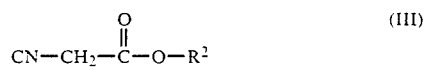

in which
$R^2$ represents alkyl, in the presence of a base and if appropriate in the presence of a diluent, and the Δ²-pyrroline-2-carboxylic acid derivatives thus obtainable, of the formula (IVa)

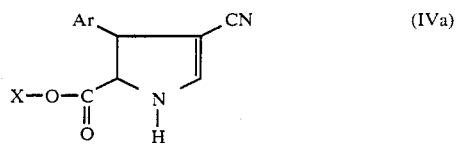

in which
X represents hydrogen or an equivalent of an inorganic or organic cation and
Ar has the abovementioned meaning, are oxidatively decarboxylated in a 2nd step if appropriate in the presence of a base and in the presence of a metal salt and also if appropriate in the presence of a diluent.

It is to be considered as extremely surprising that the cyclization of a-cyanoacrylic acid derivatives of the formula (II) with isocyanoacetic acid esters of the formula (III) leads to Δ²-pyrroline-2-carboxylic acid derivatives, since on the basis of the prior art it was to be expected that under the given reaction conditions hydrogen cyanide would be preferably eliminated in the cyclization of the compounds and pyrrole derivatives rather than pyrroline derivatives should result from this (compare JP No. 59/212,468) Moreover, it is also completely surprising that the oxidative decarboxylation of the Δ²-pyrroline-2-carboxylic acid derivatives carried out in the 2nd step of the process according to the invention occurs under mild conditions of this type in the presence of a copper-II salt catalyst, since it was known from the prior art that copper-II salts alone are not able to effect oxidative decarboxylation under mild reaction conditions (compare Organic Reactions vol. 19, p. 279, 303 et seq.).

A particular advantage of the process according to the invention consists in the use of readily available economical starting materials; moreover, the fact that products of high purity are obtained in good yields without expensive purification operations represents a further advantage of the process according to the invention.

Formula (I) provides a general definition of the 3-cyano-4-aryl-pyrroles obtainable with the aid of the process according to the invention.

Compounds of the formula (I) which can preferably be prepared are those in which Ar represents pyridyl, furyl or thienyl which are optionally monosubstituted to polysubstituted in each case by identical or different substituents from the group comprising halogen and straight-chain or branched alkyl having 1 to 4 carbon atoms or represents phenyl which is optionally monosubstituted to polysubstituted by identical or different substituents, suitable substituents being halogen, cyano, nitro, in each case straight-chain or branched alkyl, alkoxy, alkylthio or alkoxycarbonyl, having in each case 1 to 4 carbon atoms, in each case straight-chain or branched halogenoalkyl, halogenoalkoxy or halogenoalkylthio, having in each case 1 to 4 carbon atoms and 1 to 9 identical or different halogen atoms and also bivalent dioxyalkylene having 1 or 2 carbon atoms, optionally substituted by fluorine.

Compounds of the formula (I) which can particularly preferably be prepared are those in which Ar represents 2-pyridyl, 4-pyridyl, 2-furyl or 2-thienyl which are in each case optionally monosubstituted or disubstituted by identical or different substituents from the group comprising fluorine, chlorine, bromine, methyl and ethyl or represents phenyl which is optionally monosubstituted, disubstituted or trisubstituted by identical or different substituents, suitable substituents being: fluorine, chlorine, bromine, methyl, ethyl, n- or i-propyl, methoxy, ethoxy, methylthio, trifluoromethyl, trifluoromethoxy, trifluoromethylthio, cyano, nitro, dioxymethylene and dioxydifluoromethylene.

Compounds of the formula (I) which can very particularly preferably be prepared are those in which Ar represents phenyl which is optionally monosubstituted or disubstituted by identical or different substituents, suitable substituents being: fluorine, chlorine, bromine, methyl, ethyl, methoxy, ethoxy, methylthio, trifluoromethyl, trifluoromethoxy, trifluoromethylthio, nitro and dioxydifluoromethylene.

If, for example, ethyl 2-(2,3-dichlorophenyl-methylidene)-cyanoacetate and ethyl isocyanoacetate are used as starting materials, then the course of the reaction of the process according to the invention can be represented by the following equation:

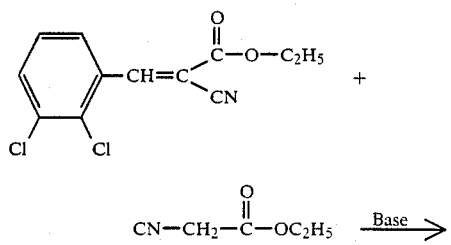

$$CN-CH_2-\overset{O}{\underset{\|}{C}}-OC_2H_5 \xrightarrow{\text{Base}}$$

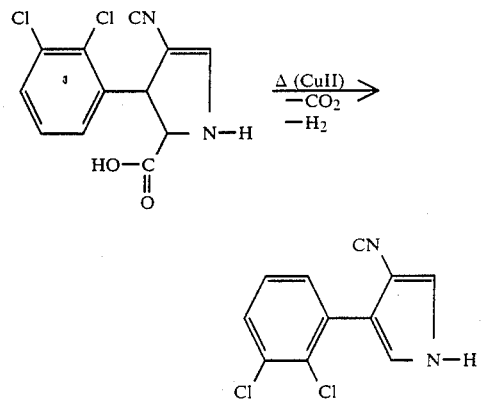

Formula (II) provides a general definition of the α-cyanoacrylic acid derivatives required as starting materials for carrying out the process according to the invention. In this formula (II), Ar preferably represents those radicals which have already been mentioned as preferable for this substituent in connection with the description of the substances which can be prepared according to the invention, of the formula (I).

$R^1$ preferably represents straight-chain or branched alkoxy having 1 to 4 carbon atoms, in particular methoxy and ethoxy, or represents amino.

The α-cyanoacrylic acid derivatives of the formula (II) have been disclosed (compare, for example, J6-1030-571 or J6-1200-984) or can be prepared analogously to known processes (compare also J. Chem. Soc. 1961, 683,) for example when aldehydes of the formula (V)

in which

Ar has the abovementioned meaning, are condensed with cyanoacrylic acid derivatives of the formula (VI)

in which $R^1$ has the abovementioned meaning, if appropriate in the presence of a diluent such as, for example, ethanol and if appropriate in the presence of a base such as, for example, potassium hydroxide or piperidine at temperatures between +20° C. and +150° C.

The aldehydes of the formula (V) and the cyanoacetic acid derivatives of the formula (VI) are generally known compounds of organic chemistry.

Formula (III) provides a general definition of the isocyanoacetic acid esters furthermore required as starting materials for carrying out the process according to the invention. In this formula (III), $R^2$ preferably represents straight-chain or branched alkyl having 1 to 4 carbon atoms, in particular methyl or ethyl.

The isocyanoacetic acid esters have been disclosed (compare, for example, JP No. 59/212,468 and also Liebigs Ann. Chem. 763, 1, [1972]).

Inert organic solvents are suitable as diluents for carrying out the 1st step of the process according to the invention. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl- or-diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, sulphoxides, such as dimethyl sulphoxide or alcohols, such as methanol or ethanol.

The 1st step of the process according to the invention is preferably carried out in the presence of a suitable base. All customarily utilizable inorganic and organic bases are suitable for this. Hydrides, hydroxides, amides, alcoholates, carbonates or hydrogen carbonates of alkali metals, such as, for example, sodium hydride, sodium amide, sodium hydroxide, sodium methylate, sodium ethylate, potassium t-butylate, sodium carbonate or sodium hydrogen carbonate and also tertiary amines, such as, for example, triethylamne, N,N-dimethylaniline, pyridine, N,N-dimethylaminopyridine, diazabicyclooctane (DABCO), diazabicyclononene (DBN) or diazabicycloundecene (DBU) are preferably used. Potassium hydroxide is used with particular preference as the base.

The reaction temperatures can be varied within a relatively wide range in carrying out the 1st step of the process according to the invention. In general, the reaction is carried out at temperatures between $-20°$ C. and $+100°$ C., preferably at temperatures between $0°$ C. and $50°$ C.

For carrying out the 1st step of the process according to the invention, 1.0 to 2.0 mols, preferably 1.0 to 1.2 mols, of isocyanoacetic acid ester of the formula (III) and if appropriate 1.0 to 6.0 mols, preferably 2.0 to 3.0 mols of base are generally employed per mol of α-cyanoacrylic acid derivative of the formula (II). Carrying out the reaction, working up and isolation of the reaction products are by generally customary methods (compare also the preparation examples).

If the 1st step of the process according to the invention is carried out at a low temperature ($-20°$ C. to $+30°$ C.) in an aprotic diluent such as, for example, tetrahydrofuran or dimethylformamide and if only a small molar excess of hydroxide base or anhydrous organic bases such as, for example, potassium t-butylate are used, then the $\Delta^2$-pyrroline-2-carboxylic acid esters occurring as by-products of the formula (IVb)

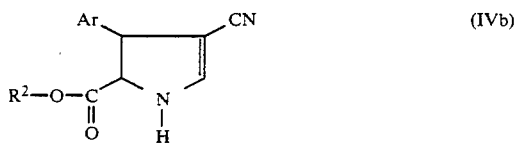

in which
R$^1$ represents alkyl, in particular methyl or ethyl, and Ar has the abovementioned meaning, occurring as intermediates in the reaction can be isolated.

They can then be hydrolyzed to the intermediates of the formula (IVa) in the customary manner in a separate reaction step.

However, a reaction procedure is preferred in the 1st step of the process according to the invention in which the intermediates of the formula (IVb) are not isolated.

Inert organic solvents are suitable as diluents for carrying out the 2nd step of the process according to the invention. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, alcohols, such as methanol or ethanol, or mixtures thereof with water.

The 2nd step of the process according to the invention is preferably carried out in the presence of a suitable heavy metal salt. Cu-I or Cu-II salts such as cooper acetate or copper chloride or iron-III salts such as, for example, iron-III chloride are used with particular preference.

The 2nd step of the process according to the invention is preferably carried out in the presence of a suitable base. All customary inorganic or organic bases are suitable for this. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a relatively wide range in carrying out the 2nd step of the process according to the invention. In general, the reaction is carried out at temperatures between $0°$ C. and $150°$ C., preferably at temperatures between $20°$ C. and $120°$ C.

For carrying out the 2nd step of the process according to the invention, 0.01 to 3.0 moles, preferably 0.1 to 0.5 moles, of metal salt and 0.1 to 3.0 moles, preferably 1.0 to 1.5 moles, of base are generally employed per mole of $\Delta^2$-pyrroline-2-carboxylic acid derivative of the formula (IVa).

If the metal salt is only employed in catalytic amounts, then it is advantageous to introduce in addition air or pure oxygen into the reaction mixture in order further to oxidize reduced metal ions. Carrying out of the reaction, working up and isolation of the reaction products are by the generally customary methods (compare also the preparation examples).

The compounds of the formula (I) obtainable with the aid of the process according to the invention are known compounds which find use as fungicides or microbicides and as intermediates for the synthesis of further fungicides or microbicides (compare, for example, EP No. 96,142, EP No. 111,452; DE-OS German Published Specification) No. 2,927,480).

The intermediates of the formula (IV)

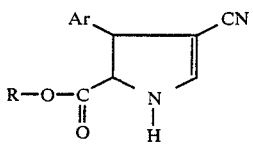 (IV)

in which

R represents hydrogen, alkyl or an equivalent of an inorganic or organic cation; preferably hydrogen, straight-chain or branched alkyl having 1 to 4 carbon atoms or one equivalent of an alkali metal cation, an alkaline earth metal cation or optionally substituted ammonium cation; in particular hydrogen, methyl, ethyl or an equivalent of a sodium, potassium or ammonium ion and also a mono-, di- or trialkylammonium ion (having in each case 1 to 4 carbon atoms in each case in the separate alkyl parts) and Ar has the abovementioned meaning, are new and are also the subject of the present invention. In addition to their valuable properties as intermediates for the synthesis of fungicidal or microbicidal active compounds, they also possess fungicidal and microbicidal properties themselves.

For such purposes they can be formulated and applied as described in U.S. Pat. No. 4,663,327.

PREPARATION EXAMPLES

Example 1

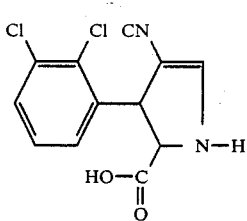 (IVa-1)

A suspension of 4.8 g (0.02 mol) of 2-cyano-3-(2,3-dichlorophenyl)acrylamide in 50 ml of ethanol is added to 2.4 g (0.04 mol) of potassium hydroxide in 100 ml of ethanol at −5° C. to 10° C., then 2.6 g (0.022 mol) of ethyl isocyanoacetate is added dropwise and the mixture is stirred at room temperature for 4 hours after completion of the addition. For working up, 200 ml of water are added, the mixture is extracted using ethyl acetate, the organic phase is discarded and the aqueous phase is acidified using 1 normal hydrochloric acid and extracted a second time using ethyl acetate. By the addition of petroleum ether, a solid is obtained from the combined ethyl acetate phases of the 2nd extraction which, after filtering off and drying, possesses a melting point of 200° C. to 202° C. and possesses a purity of 95% according to the high pressure liquid chromatogram.

$^1$H-NMR (DMSO-d$_6$/TMS): δ=4.3 (d, 1H); 4.8 (d, 1H); 7.3 (d, 1H); 7.4 (t, 1H); 7.5 (s, 1H); 7.6 (m, 2H); 13.0–13.5 (m, 1H) ppm.

$^{13}$C-NMR (DMSO-d$_6$): δ=48.3; 67.1; 77.9; 118.9; 127.7;129.0; 129.8; 130.6; 132.3; 141.7; 152.7; 172.4 ppm.

MS: m/e=282 (M$^+$)

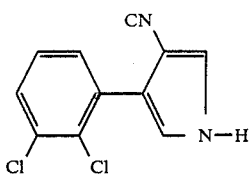 (I-1)

5.6 g (0.02 mol) of 3-(2,3-dichlorophenyl)-4-cyano-Δ$^2$-pyrroline-2-carboxylic acid are added with stirring at room temperature to a mixture of 2 g (0.01 mol) of copper acetate monohydrate and 2 ml (0.025 mol) of pyridine in 100 ml of a toluene/ethyl acetate mixture (1:1), and the reaction mixture is then heated to reflux for 6 hours. After cooling, insoluble components are filtered off, and the reaction mixture is washed successively with 1 normal hydrochloric acid, aqueous sodium carbonate solution and water, dried over sodium sulphate and concentrated in vacuo After digestion of the residue with diisopropyl ether, 3-cyano-4-(2,3-dichlorophenyl)-pyrrole is obtained as a solid of melting point 14920 C.-150° C., having a purity of 98% as determined by gas chromatography.

$^1$H-NMR (DMSO-d$_6$/TMS): δ=7.2 (d, 1H); 7.4–7.5 (m, 2H) 7.65 (m, 1H); 7.75 (d, 1H) ppm.

Preparation of the intermediates (IVb)

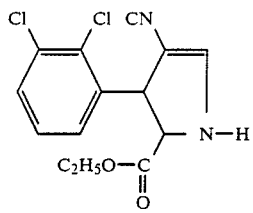 (IVb-1)

A solution of 4.8 g (0.02 mol) of 2-cyano-3-(2,3-dichlorophenyl)acrylamide and 2.5 g (0.022 mol) of ethyl isocyanoacetate in 60 ml of a tetrahydrofuran/dimethylformamide mixture (5:1) are added dropwise with stirring to a suspension of 2.4 g (0.021 mol) of potassium t-butylate in mI of tetrahydrofuran at 0° C. to 10° C. After completion of the addition, the reaction mixture is stirred for a further 5 hours at room temperature then poured into 250 ml of water and extracted these times with diethyl ether, and the combined ether phases washed with water, dried over sodium sulphate and concentrated in vacuo, The oily residue is purified by chromatography on silica gel (eluent: ethyl acetate/cyclohexane) and digestion with diisopropyl ether. The ethyl 3-cyano-4-(2,3-dichlorophenyl)-Δ$^2$-pyrroline-5-carboxylate thus obtainable has a melting point of 124° C.-125° C., $^1$H-NMR (CDCl$_3$/TMS): δ=1.3 (t, 3H; 4.2 (d, 1H); 4.3 (m, 2H); 5.=(d, 1H); 7.1–7.3 (m, 4H); 7.4 (m, 1H) ppm.

MS: m/e=310 (M$^+$)

The following examples are obtained in a corresponding manner and in accordance with the general instructions for preparation:

| Example IVa-2 | 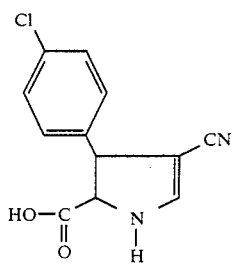 | melting point 180°–181° C. |

| Example IVb-2 | 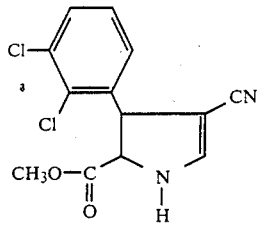 | melting point 154°–156° C. |

It is understood that the specification and examples are illustrative but not limitative of the present invention and that other embodiments within the spirit and scope of the invention will suggest themselves to those skilled in the art.

I claim:

1. A pyrrole-2-carboxylic acid derivative of the formula

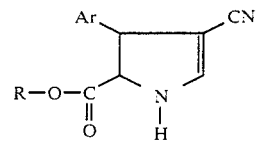

in which

R is hydrogen, alkyl or an equivalent of an inorganic or organic cation, and

Ar is optionally substituted heteroaryl or aryl.

* * * * *

UNITED STATES PATENT AND TRADEMARK OFFICE
CERTIFICATE OF CORRECTION

PATENT NO. : 4,923,994

DATED : May 8, 1990

INVENTOR(S) : Detlef Wollweber

It is certified that error appears in the above-identified patent and that said Letters Patent is hereby corrected as shown below:

Title Page      ABSTRACT: 3rd line from bottom after " carboxylic " delete " -pyrroline-2-carboxylic "

Col. 10, claim 1 line 32      After " aryl " insert -- selected from the group consisting of pyridyl, furyl, or thienyl (which are unsubstituted or mono or polysubstituted by halogen or lower alkyl) or phenyl which is unsubstituted or substituted by halogen, cyano, nitro, lower alkyl, lower alkoxy, lower alkylthio, lower alkoxycarbonyl, lower halogenoalkyl, lower halogenoalkoxy, lower halogenoalkylthio or bivalent dioxyalkylene having 1 or 2 carbon atoms which may be substituted by fluorine --

Signed and Sealed this

Eighteenth Day of February, 1992

Attest:

HARRY F. MANBECK, JR.

*Attesting Officer*      *Commissioner of Patents and Trademarks*